(12) United States Patent
McMichael

(10) Patent No.: US 6,592,875 B1
(45) Date of Patent: *Jul. 15, 2003

(54) METHOD FOR TREATMENT OF LYME DISEASE

(75) Inventor: John McMichael, Delanson, NY (US)

(73) Assignee: Milkhaus Laboratory, Inc., Delanson, NY (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/556,715

(22) Filed: Apr. 21, 2000

Related U.S. Application Data

(60) Provisional application No. 60/140,089, filed on Jun. 21, 1999.

(51) Int. Cl.[7] ........................ A61K 39/02; A61K 39/08; C12N 11/00

(52) U.S. Cl. .................. 424/234.1; 424/9.2; 424/93.4; 424/184.1; 435/174

(58) Field of Search ................... 424/9.2, 93.4, 424/184.1, 234.1; 435/174

(56) References Cited

U.S. PATENT DOCUMENTS

| | | | |
|---|---|---|---|
| 5,178,859 A | | 1/1993 | Simon et al. ............... 424/85.8 |
| 5,582,829 A | * | 12/1996 | Alliger et al. ............ 424/88.92 |
| 5,688,512 A | * | 11/1997 | Bergstrom et al. ........ 424/234.1 |
| 5,807,685 A | | 9/1998 | Flavell et al. ................ 435/7.1 |

* cited by examiner

*Primary Examiner*—Rodney P Swartz
(74) *Attorney, Agent, or Firm*—Marshall, Gerstein & Borun

(57) ABSTRACT

The present invention relates to a treatment for patients having Lyme disease by administering a composition comprising an *Borrelia burgdorferi* antigen at a sub-vaccine level effective to alleviate symptoms of Lyme disease.

**6 Cla

METHOD FOR TREATMENT OF LYME DISEASE

This application claims priority on provisional patent application Serial No. 60/140,089 filed Jun. 21, 1999.

BACKGROUND OF THE INVENTION

This invention relates generally to the treatment of Lyme Disease and compositions for use therein.

Lyme Disease is a tick-bourne multisystem inflammatory disorder caused by the spirochete *Borrelia burgdorferi*. The disorder was first recognized in 1975 because of a clustering of cases in Lyme Connecticut. In the United States, the white-footed mouse and deer are the preferred hosts for the immature and adult ticks (*I. dammini*), respectively.

The disease is divided into early disease (stages 1 and 2) and late disease (stage 3). Stage 1 is characterized by the presence of a distinctive skin lesion, erythema migrans. Stage 2 is a disseminated phase of the infection, with manifestations in the skin, CNS, musculoskeletal system and heart. Late disease, or stage 3 reflects persistent infection that is clinically manifest for more that one year after onset. Common clinical features include carditis, neurologic abnormalities and arthritis.

Treatment of active Lyme disease consists of administration of appropriate antibiotics although treatment of acute disease is reported to be more successful than treatment of chronic disease. Early studies indicated that oral tetracycline treatment of early localized Lyme disease reduces the likelihood of later neurologic, cardiac and rheumatic complications. Doxcycline is currently the drug of choice for this early stage. Administration of ceftriaxone is recommended for treatment of the cardiac, neurologic, and rheumatologic manifestations of disseminated and persistent Lyme disease.

The most practical means of preventing Lyme disease is to minimize exposure to ticks by wearing protective clothing, using acaricides and avoiding the habitat of the host vectors. Recently, a vaccine comprising a recombinant *B. burgdorferi* outer-surface lipoproteins (Osp A) has been tested in animals and in humans. This Lyme disease vaccine (LYMErix™, SmithKline Beecham Biologicals) has been shown to serve as a protective antigen in animals and as a safe immunogen in humans. The LYMEriX™ vaccine is administered at a dosage of 30 micrograms of recombinant Osp A lipoprotein at 0, 1 and 12 months with all three doses required to achieve optimal protection. *B. burgdoiferi* expresses OspA while residing in the midgut of the infected tick, but OspA is down regulated after tick attachment and is usually undetectable or absent when *B. Burgdorferi* is inoculated into the human host. Schwan et al. Proc. Natt. Acad. Sci. (USA) 92/;2909–2913 (1995). Therefore, a novel hypothesis has been proposed to explain the effectiveness of lipoprotein OspA vaccination. When infected ticks bite humans who have been vaccinated with recombinant OspA, the vaccine-induced antibodies are taken up by the tick and interact with the *B. Burgdorferi* in the midgut of the tick, thereby preventing transmission of the organism to the host. This mechanism has been suggested by a pre-clinical study in which *B. Burgdorferi* were detected by immunofluorescence assay in none of the ticks that fed on OspA-immunized mice, compared with 72% of ticks that fed on control-immunized mice. Fikrig et al. Proc. Natl. Acad. Sci. (USA) 89:5418–5421 (1992).

Despite such advances in prevention of Lyme disease there still remains a need for improved methods of treatment for the disease.

SUMMARY OF THE INVENTION

The invention provides methods for treating a patient suffering from Lyme disease comprising the step of: administering a composition comprising a *Borrelia burgdorferi* antigen at a sub-vaccine level effective to alleviate symptoms of Lyme disease. Suitable antigens for use according to the invention include outer surface lipoproteins of *Borrelia burgdorferi* such as the outer surface lipoproteins OspA, OspB, OspC and the antigen LFA-a. A preferred antigen for use according to the invention is lysed *Borrelia burgdorferi* produced by treatment of the organism in phenol followed by multiple freeze/thaw cycles. Borrelia burgdorferi for use according to the invention is publically available as ATCC deposit 35210.

The *Borrelia burgdorferi* antigens are administered at sub-vaccine levels. Sub-vaccine levels are defined as levels less than those sufficient to induce an effective humoral immune response as exemplified by the determination of a positive wheal upon subcutaneous injection. According to one aspect of the invention, the composition comprises from about $0.5 \times 10^{-6}$ g to about $0.02 \times 10^{-6}$ g of the outer surface lipoprotein per dose and from one to four doses are administered daily. More preferably, the composition is administered at a dosage of about $0.1 \times 10^{-6}$ g of the outer surface lipoprotein. The compositions of the invention may be administered to patients by a variety of suitable methods with means selected from the group consisting of sublingual, subcutaneous, intravenous, intramuscular, and intrathecal administration being preferred. Particularly preferred methods of administration are sublingual and subcutaneous methods of administration. When the composition is administered sublingually, it is preferred that four doses be administered daily. When the composition is administered by injection such as subcutaneously, it is preferred that it be administered in a single daily dose.

According to one preferred method the composition is administered to a patient in a single dose of about 0.05 cc in a pharmaceutically acceptable carrier. Such pharmaceutically-acceptable carriers include water, saline, albumin, and dextrose and combinations thereof.

Compositions of the invention for treatment of the symptoms of Lyme disease comprise *Borrelia burgdorferi* antigens at a sub-vaccine level effective to alleviate symptoms of Lyme disease in a pharmaceutically acceptable carrier. Preferred are compositions which comprise from about $0.5 \times 10^{-6}$ g to about $0.02 \times 10^{-6}$ g of the *Borrelia burgdorferi* per dose with those comprising about $0.1 \times 10^{-6}$ g of the *Borrelia burgdorferi* per dose being most preferred.

Additional aspects and advantages of the invention will become apparent upon consideration of the following detailed description thereof.

DETAILED DESCRIPTION OF THE INVENTION

The present invention relates to the discovery that the administration of *Borrelia burgdorferi* antigens at a sub-vaccine levels is effective to alleviate symptoms of Lyme disease. While not wishing to be bound by a particular theory of invention, it is believed that many of the symptoms of Lyme Disease result as a consequence of a hypersensitivity reaction to *Borrelia burgdorferi* that becomes an auto-immune disorder. The therapy of the invention functions to interrupt the hypersensitivity reaction by inducing suppressor T cells that shut down effector cells (helper T cells, mast cells and killer T cells) that promote the auto-immune response.

The following Examples illustrate the preferred embodiments of the invention and provide evidence of the effectiveness of claimed treatment methods. In addition to the patients described in Examples 1 and 2 about four other patients suffering from Lyme disease have been treated and shown similar results with no adverse side effects. Numerous improvements and further aspects of the invention are apparent to the skilled artisan upon consideration of the Examples which follow.

EXAMPLE 1

According to this example, a 45 year old female suffering from chronic Lyme disease of nearly one year's duration was treated according to the methods of the invention. Previous treatment with antibiotics, steroids, and other analgesics provided only temporary relief from symptoms of arthritis. The patient who was treated by sublingual administration four times daily of one drop (0.05 mL) of a composition comprising a 1:25 dilution of a commercially available recombinant OspA Lyme disease vaccine (LYMErix™, SmithKline Beecham Biologicals). The diluted composition comprises $0.12 \times 10^{-6}$ g of recombinant lipoprotein OspA adsorbed onto aluminum as aluminum hydroxide adjuvant in phosphate buffered saline further comprising 2-phenoxyethanol as a bacteriostatic agent.

After two weeks treatment according to the method of the invention the subject was nearly pain free, and was able to remain active all day and generally experienced a much improved quality of life. The patient has not experienced any adverse effects.

EXAMPLE 2

According to this example, a 71 year old female with chronic Lyme disease was treated according to the methods of the invention. The patient suffered from nearly incapacitating pain which was refractory to other medications was treated by sublingual administration of four times daily of from three to seven drops (0.05 mL per drop) of the composition of Example 1. The patient showed dramatic improvement in her symptoms after one month and has not experienced any adverse effects.

The invention has been described in terms of its preferred embodiments and is only intended to be limited-by the scope of the following claims.

What is claimed:

1. A method for treating a patient suffering from Lyme disease comprising the step of:

administering a composition comprising a *Borrelia burgdorferi* antigen effective to alleviate symptoms of Lyme disease, wherein said composition comprises from $0.5 \times 10^{-6}$ g to $0.02 \times 10^{-6}$ g of *Borrelia burgdorferi* outer surface lipoprotein per dose.

2. The method of claim 1 wherein said composition is administered to a patient in a single dose of about 0.05 cc in a pharmaceutically acceptable carrier.

3. The method of claim 1 wherein multiple daily doses of said composition are administered to the patient.

4. The method of claim 1 where the composition is administered to a patient by a means selected from the group consisting of sublingually, subcutaneously, intravenously, intramuscularly, and intrathecally.

5. The method of claim 4, wherein the composition is administered to a patient sublingually.

6. A composition for treatment of the symptoms of Lyme disease comprising a *Borrelia burgdorferi* antigen effective to alleviate symptoms of Lyme disease in a pharmaceutically acceptable carrier, wherein the composition comprises from $0.5 \times 10^{-6}$ g to $0.02 \times 10^{-6}$ g of *Borrelia burgdorferi* outer surface lipoprotein per dose.

* * * * *